US00PP22692P3

(12) United States Plant Patent
NeSmith

(10) Patent No.: US PP22,692 P3
(45) Date of Patent: May 1, 2012

(54) BLUEBERRY PLANT NAMED 'SOUTHERN SPLENDOUR'

(50) Latin Name: ***Vaccinium* hybrid**
Varietal Denomination: Southern Splendour

(75) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/802,984

(22) Filed: Jun. 17, 2010

(65) Prior Publication Data

US 2011/0314578 P1 Dec. 22, 2011

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP16,756 P3 7/2006 NeSmith
PP18,138 P3 10/2007 NeSmith

*Primary Examiner* — Susan McCormick Ewoldt
(74) *Attorney, Agent, or Firm* — Davis Wright Tremaine LLP; Dale C. Hunt

(57) ABSTRACT

A new and distinct cultivar of Southern highbush blueberry, 'Southern Splendour', is provided. 'Southern Splendour' is a *Vaccinium* hybrid, which is characterized by high vigor, short fruit ripening period, and high quality fruit suitable for mechanical harvesting.

4 Drawing Sheets

Latin name of the genus and species of the plant claimed: 'Southern Splendour' is a southern highbush blueberry plant that is a *Vaccinium* hybrid.

Variety denomination: The new southern highbush blueberry plant claimed is of the variety denominated 'Southern Splendour'.

BACKGROUND OF THE INVENTION

The present invention relates to the discovery of a new and distinct cultivar of southern highbush blueberry (*Vaccinium* hybrid) plant. The parents of the new variety are Palmetto and Reveille. The male parent of the new *Vaccinium* plant variety 'Southern Splendour' is 'Palmetto' (U.S. Plant Pat. No. 16,756). The female parent of the new *Vaccinium* plant variety 'Southern Splendour' is Reveille, which is a non-patented variety released by North Carolina State University in 1990. The new plant variety 'Southern Splendour' has been evaluated and tested in Waycross, Ga. and Griffin, Ga.

The new *Vaccinium* plant variety 'Southern Splendour' has been shown to maintain its distinguishing characteristics through successive asexual propagations by, for example, softwood cuttings. Plants from softwood cuttings have been directly planted in the ground. Clones propagated from cuttings have maintained the vegetative and fruit characteristics of the original selection. The original means of asexual reproduction was a seedling derived from the cross of Palmetto and Reveille. From the original plant, softwood cuttings were taken in Griffin, Ga. in 2001 to multiply the original. Subsequent propagations were made from those plants via softwood propagation in the years to follow as needed. All softwood cuttings appeared true to type, with no deviations observed.

'Southern Splendour' has been compared with southern highbush cultivars 'Rebel' (U.S. Plant Pat. No. 18,138), 'Palmetto' (U.S. Plant Pat. No. 16,756), and 'Reveille' (not patented). The fruit of 'Southern Splendour' is larger than the fruit of 'Palmetto.' The fruit development period of 'Southern Splendour' is 54 to 58 days, shorter than the fruit development period of 'Palmetto', which is 65-69 days.

The chilling requirement of 'Southern Splendour' is 450 to 500 hours of temperatures at or below 7 C, compared to 350 to 400 hours for 'Palmetto' and over 700 hours for 'Reveille'. The cold hardiness of 'Southern Splendour' is similar to 'Star' and 'Rebel'. Resistance to diseases of 'Southern Splendour' is also similar to 'Star', 'Rebel', and 'Palmetto', with no exceptional disease resistance or susceptibility observed.

SUMMARY OF THE INVENTION

The new Southern highbush blueberry plant variety 'Southern Splendour' has not been observed under all possible environmental conditions. The phenotype may vary somewhat with variations in environment and cultural practices such as temperature and light intensity without, however, any variance in genotype.

The following traits have been repeatedly observed at Waycross, Ga. and Griffin, Ga. and are determined to be the unique characteristics of the new plant variety 'Southern Splendour':

1. High vigor.
2. Short fruit ripening period.
3. High quality fruit suitable for mechanical harvesting.

The fruit of 'Southern Splendour' is very firm, with a sweet aromatic flavor and very crisp texture. The storage quality is excellent and the fruit is well suited for mechanical harvesting. The fruit can be used as fresh fruit for shipping, for customer-picking and for processing markets.

BRIEF DESCRIPTION OF THE DRAWINGS

The accompanying photographic illustrations show typical specimens in full color of the flowers and fruit of the new variety 'Southern Splendour'. The colors are as nearly true as is reasonably possible in a color representation of this type.

BOTANICAL DESCRIPTION

Figure 1:
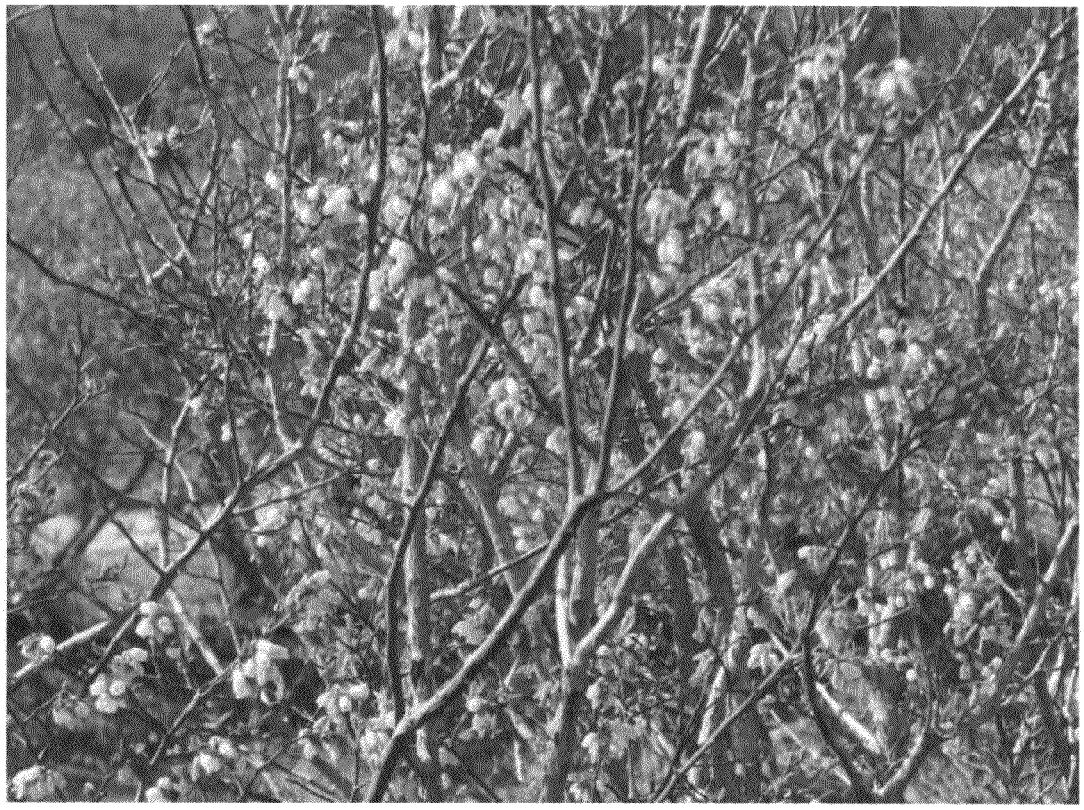
FIG. 1 is a photograph of the flower of the new variety of 'Southern Splendour'.
Figure 2:
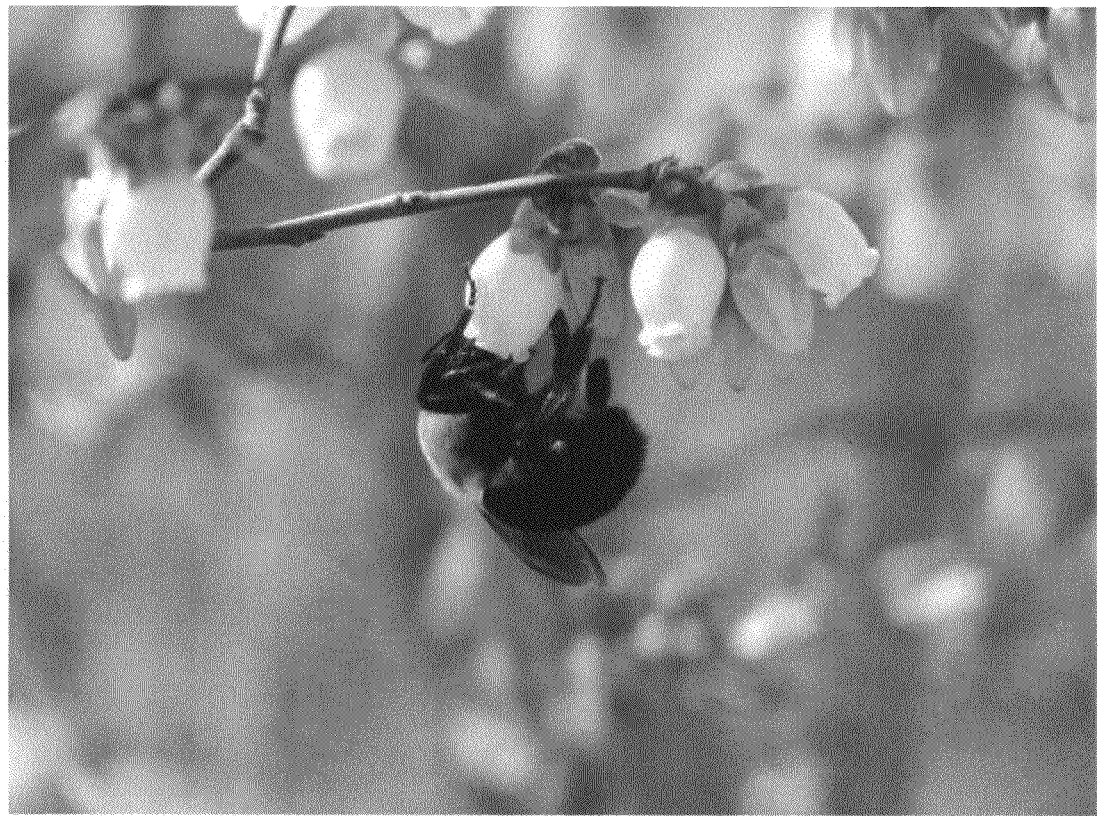
FIG. 2 is a photograph of a close-up view of the flower of the new variety of 'Southern Splendour'.
Figure 3:
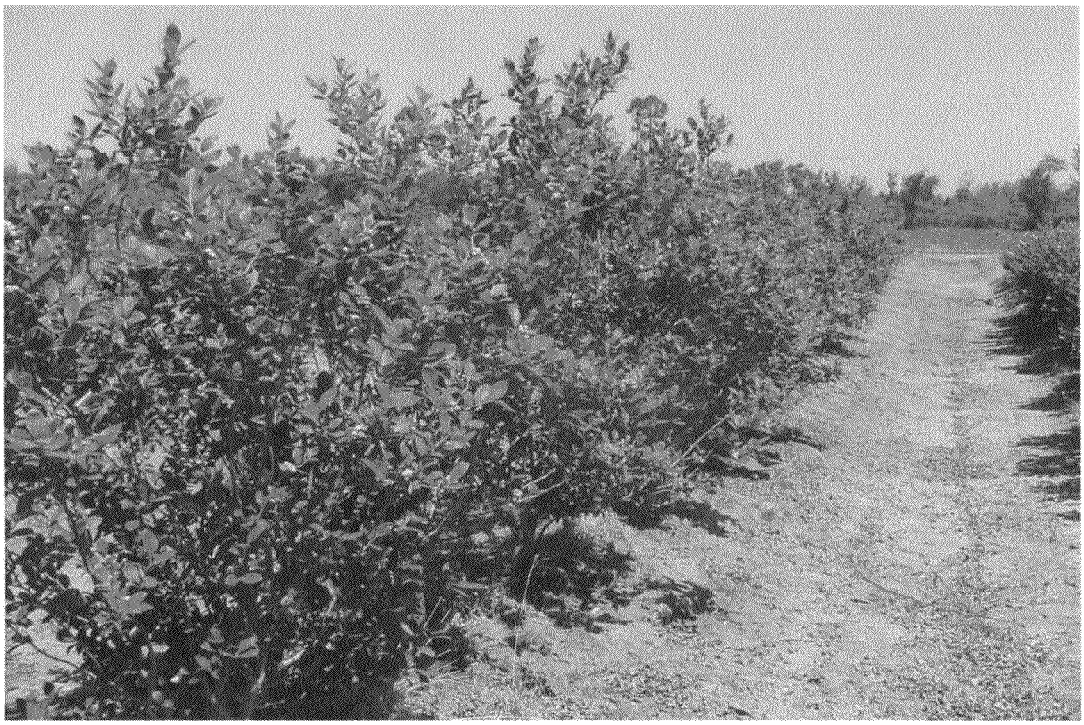
FIG. 3 is a photograph of the mature plants of the new variety of 'Southern Splendour' during fruit ripening.
Figure 4:
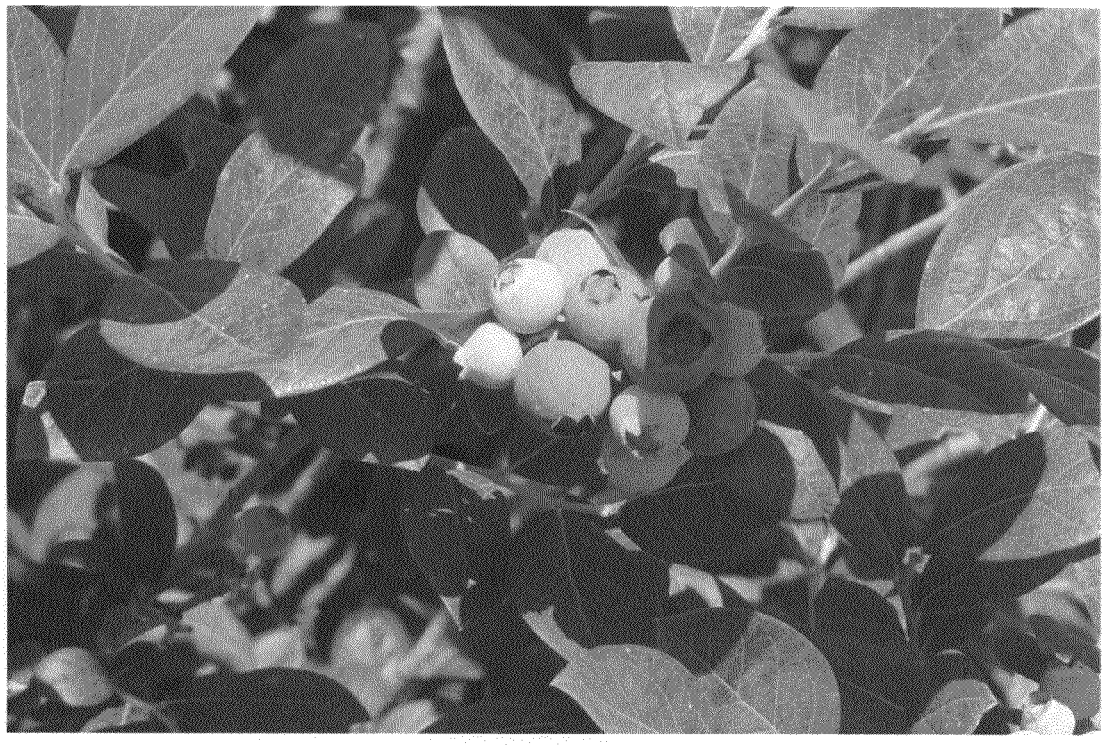
FIG. 4 is a photograph of the fruit of the new variety of 'Southern Splendour'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following is a detailed description of the botanical and pomological characteristics of the new variety 'Southern Splendour'. Where dimensions, sizes, colors, and other characteristics are given, it is to be understood that such characteristics are approximations and averages set forth as accurately as practicable. The descriptions reported herein are largely from specimen plants grown at Waycross, Ga. and Griffin, Ga. with supplemental irrigation. Data were obtained on plants that were 3 to 6 years old.

Plant:

*Habit.*—Upright, with 1 to 2 main canes arising from the crown, and multiple branching of shoots from those canes above ground.

*Size.*—1.3 to 1.5 m tall by 3 years. Plants grown under highly productive soil and fertility conditions have exceeded 2.2 m tall in 4 years. The plant crown is narrow, typically less than 30 to 45 cm in diameter. Upper portion of plant canopy exceeds 1.5 m in diameter by 3 to 4 years.

*Growth.*—Plants are highly vigorous.

*Productivity.*—Medium crop/yield. Yields of 4 to 6 lbs per plant each year on plants 3 years old or older grown under well fertilized and irrigated field conditions.

*Cold hardiness.*—Similar to other southern highbush varieties such as 'Star' and 'Rebel'.

*Chilling requirement.*—Plants require 450 to 500 hours of temperatures at or below 7 C to induce normal leafing and flowering during the spring. The chill requirement is intermediate to the male parent 'Palmetto' which is estimated to require 350 to 400 hours of chilling, and 'Reveille' which is estimated to require in excess of 700 chill hours.

*Leafing.*—Plants tend to break sufficient leaf buds simultaneously with, or shortly after, anthesis.

*Canes.*—Main cane base diameter 25 to 40 mm, color most near about Grey RHS 201D to about Brown RHS N200C; two year old cane diameter 6 to 10 mm, color transitioning from about Yellow Green RHS 146B to about Greyed Orange RHS 166B; current season wood diameter 2.5 to 3.5 mm, color about Yellow Green RHS 145B.

*Fruiting wood.*—Moderate number of twigs 10 to 15 cm in length, with internode lengths of 15 to 20 mm common.

*Disease resistance.*—No exceptional disease resistance or susceptibility observed. Typical for early season southern highbush such as 'Star', 'Palmetto', and 'Rebel'.

FOLIAGE

*Leaf color.*—Healthy mature leaves: top side of leaf color is about Green 137A, under side of leaf color is about Yellow Green 148C.

*Leaf arrangement.*—Alternate, simple.

*Leaf shape.*—Elliptic.

*Leaf margins.*—Slightly undulate to entire.

*Leaf venation.*—Reticulate.

*Leaf apices.*—Broadly acute.

*Leaf bases.*—Acute.

*Leaf dimensions.*—Length: 50 to 60 mm. Width: 25 to 35 mm.

*Leaf margins.*—Nearly smooth, occasional stalked glands along leaf margins.

*Leaf surface.*—Glaucous.

Flower:

*Date of* 50% anthesis.—3-year average March 7 to 9 in southeast Georgia; March 22 in middle Georgia.

*Flower shape.*—Urceolate.

*Flower bud number.*—Low to medium, averaging 2 to 3 buds per fruiting shoot.

*Flowers per cluster.*—5 to 8.

*Flower fragrance.*—Slight cinnamon fragrance occasionally noticed.

*Corolla color.*—As flowers first open and corollas fully expanded, a cast of about Red Purple RHS 61D is present, but flowers quickly transition to about White RHS NN155C upon opening.

*Corolla length.*—9.0 to 10.0 mm.

*Corolla width.*—5.5 to 6.0 mm.

*Corolla aperture width.*—4.0 to 4.5 mm.

*Flower peduncle.*—Length: 8.0 to 12.0 mm. Color: About Yellow Green RHS 145B.

*Flower pedicel.*—Length: 2.5 to 4.5 mm. Color: About Green RHS 138B.

*Calyx* (*with sepals*).—Diameter: 6.0 to 6.5 mm. Color: About Green RHS 137B.

*Stamen.*—Length: 5.5 to 6.0 mm. Number per flower: 10. Filament color: About Yellow Green RHS 145D.

*Style.*—Length: 8.0 to 9.0 mm. Color: About Yellow Green RHS 145B.

*Pistil.*—Length: 9.0 to 10.0 mm. Ovary color: About Green RHS 137B.

*Anther.*—Length: 3.5 to 4.0 mm. Number: 10. Color: About Greyed Orange RHS 165B.

*Pollen.*—Abundance: Medium. Color: About Yellow Orange RHS 20C. The cultivar has a low degree of self-compatibility.

Fruit:

*Date of* 50% *maturity.*—In Southeast Georgia: May 3 to 4. In Middle Georgia: May 15.

*Fruit development period.*—54 to 58 days.

*Berry color.*—With wax: About Violet Blue RHS 98D. With wax removed: About Greyed Purple RHS 187A to about Black RHS 202A.

*Berry flesh color.*—About Yellow Green RHS 145D.

*Berry surface wax abundance.*—Medium.

*Berry weight.*—First harvest: 1.6 to 1.8 g. Second harvest: 1.4 to 1.6 g.

*Berry size.*—Height from calyx to scar: 13 to 15 mm. Diameter: 15 to 18 mm.

*Berry shape.*—Nearly spherical.

*Fruit stem scar.*—Small, dry, with little or no tearing upon harvest.

*Berry firmness.*—Very firm.

*Berry flavor and texture.*—Sweet aromatic "fruity" flavor; very crisp texture.

*Storage quality.*—Excellent.

*Suitability for mechanical harvesting.*—Yes.

*Uses.*—Can be used as fresh fruit for shipping, for customer-picking and for processing markets.

Seed:

*Seed abundance in fruit.*—Low, with less than 10 fully developed seeds per berry.

*Seed color.*—About Greyed Orange RHS 165B to 165C.

*Seed dry weight.*—25.8 mg per 100 seed.

*Seed size.*—1.0 to 1.4 mm long.

What is claimed is:

1. A new and distinct variety of southern highbush blueberry plant named 'Southern Splendour', substantially as illustrated and described herein.

* * * * *